United States Patent [19]
Clyburn et al.

[11] Patent Number: 5,897,555
[45] Date of Patent: Apr. 27, 1999

[54] EXTERNAL FIXATION SYSTEM AND METHOD

[75] Inventors: Terry A. Clyburn, Houston, Tex.; Brian R. Harris, Jr., Memphis; Ben R. Shappley, Germantown, both of Tenn.

[73] Assignee: Wright Medical Technology, Inc., Arlington, Tenn.

[21] Appl. No.: 08/856,945

[22] Filed: May 15, 1997

[51] Int. Cl.⁶ .................................................. A61B 17/60
[52] U.S. Cl. .............................................. 606/54; 602/39
[58] Field of Search .................................. 606/54, 55, 56, 606/57, 58, 59, 60, 72, 73, 53; 602/39

[56] References Cited

U.S. PATENT DOCUMENTS

| | | |
|---|---|---|
| 2,080,802 | 5/1937 | Anderson . |
| 2,204,226 | 6/1940 | Wilcox . |
| 2,333,033 | 10/1943 | Mraz . |
| 4,273,116 | 6/1981 | Chiquet . |
| 4,409,970 | 10/1983 | Carrel . |
| 4,554,915 | 11/1985 | Brumfield . |
| 4,611,586 | 9/1986 | Agee et al. . |
| 4,628,919 | 12/1986 | Clyburn . |
| 4,782,842 | 11/1988 | Fietti, Jr. . |
| 4,919,119 | 4/1990 | Jonsson et al. . |
| 4,922,896 | 5/1990 | Agee et al. . |
| 5,207,676 | 5/1993 | Canadell et al. . |
| 5,391,167 | 2/1995 | Pong et al. ................................. 606/54 |
| 5,437,666 | 8/1995 | Tepic et al. ............................... 606/55 |

FOREIGN PATENT DOCUMENTS

WO 82/02830  9/1982  WIPO .

*Primary Examiner*—Guy V. Tucker
*Attorney, Agent, or Firm*—Walker, McKenzie & Walker, P.C.

[57] ABSTRACT

An external Colles' type fracture fixator which provides pivotal adjustment about three axes independently of one another and of any other movement thereof, and translational adjustment along two axes independently of one another and of any other movement thereof.

An external alignment table which allows translational adjustment along a three axes independently of one another and of any other movement thereof, and pivotal adjustment about two axes independently of one another and of any other movement thereof.

A method of externally manipulating, reducing, and stabilizing a fracture using such an external fixation alignment table and external fixator.

14 Claims, 16 Drawing Sheets

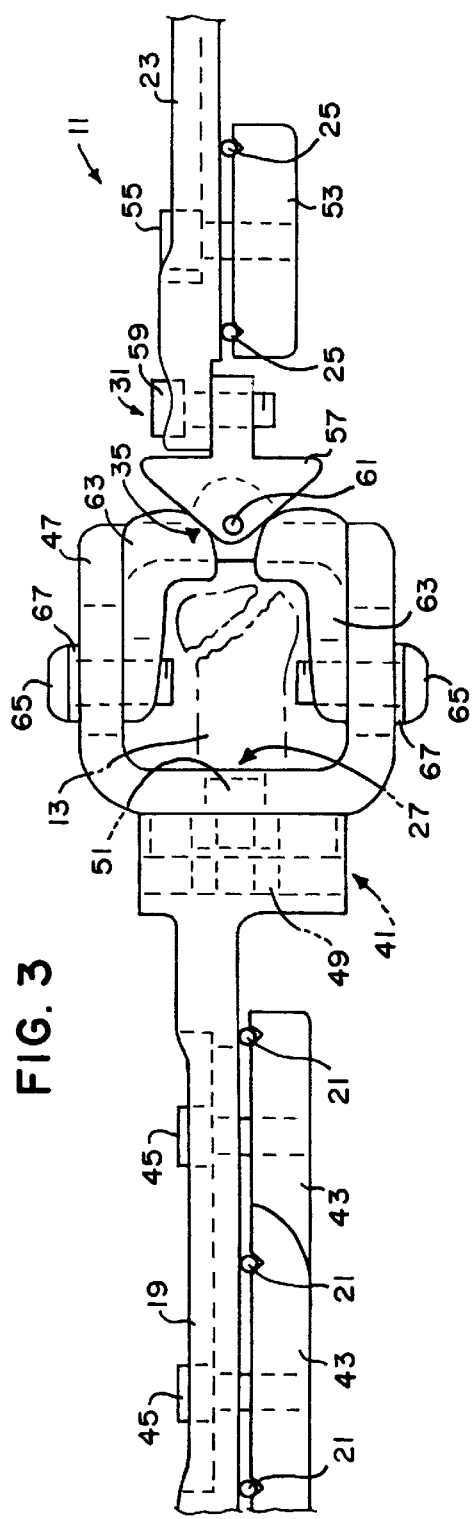
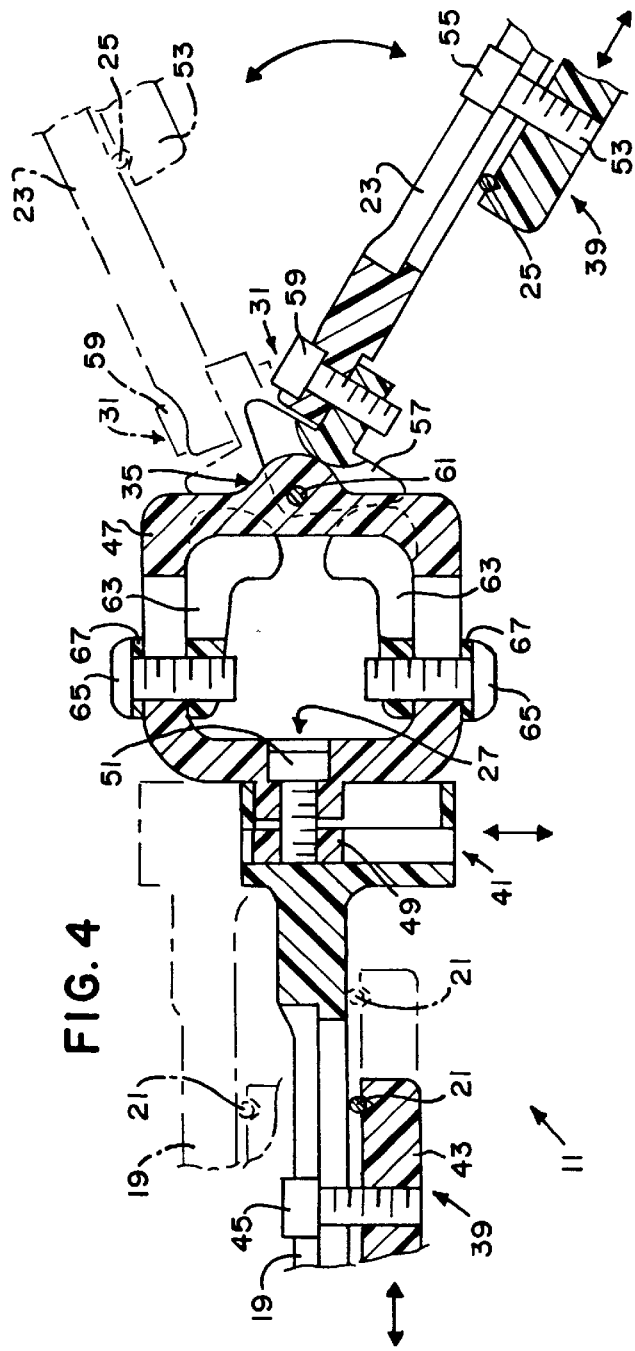
FIG. 3
FIG. 4

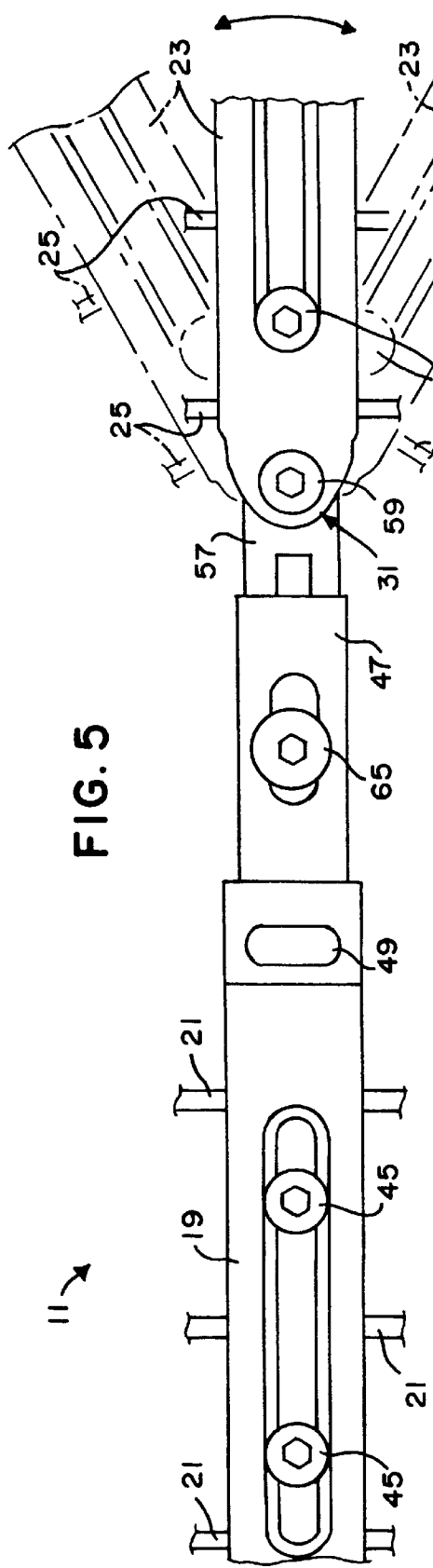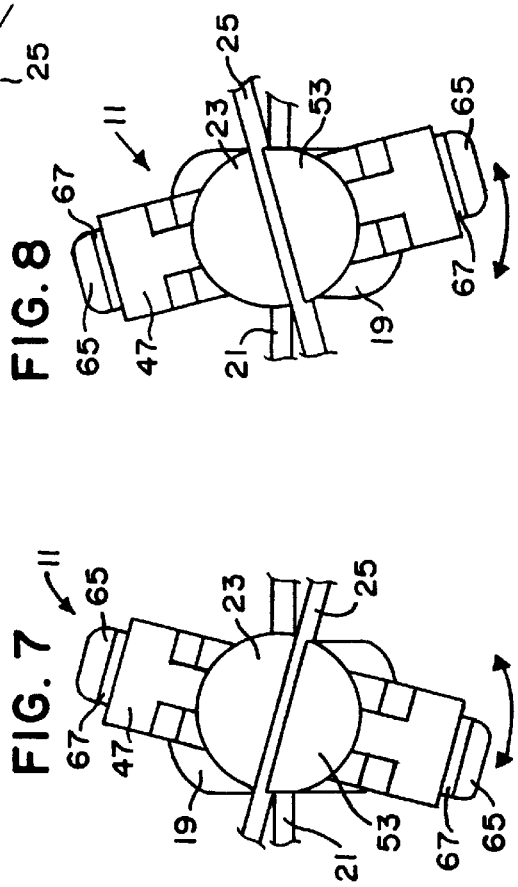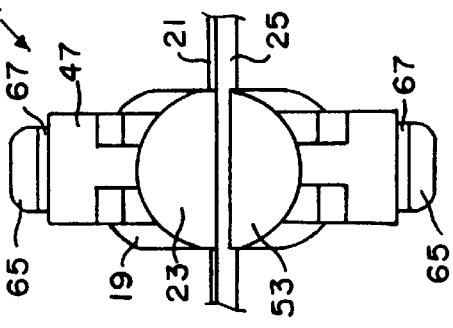

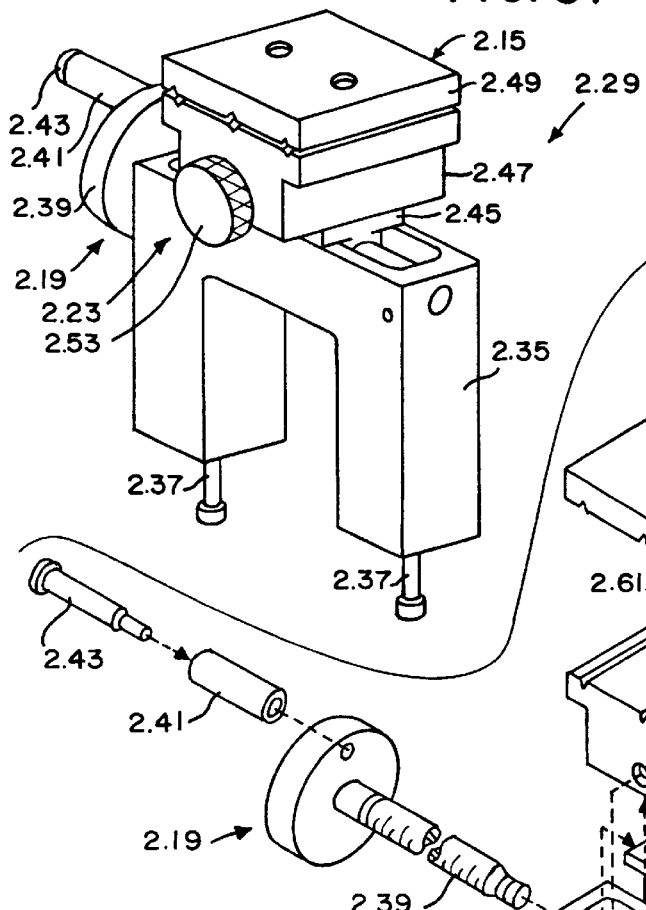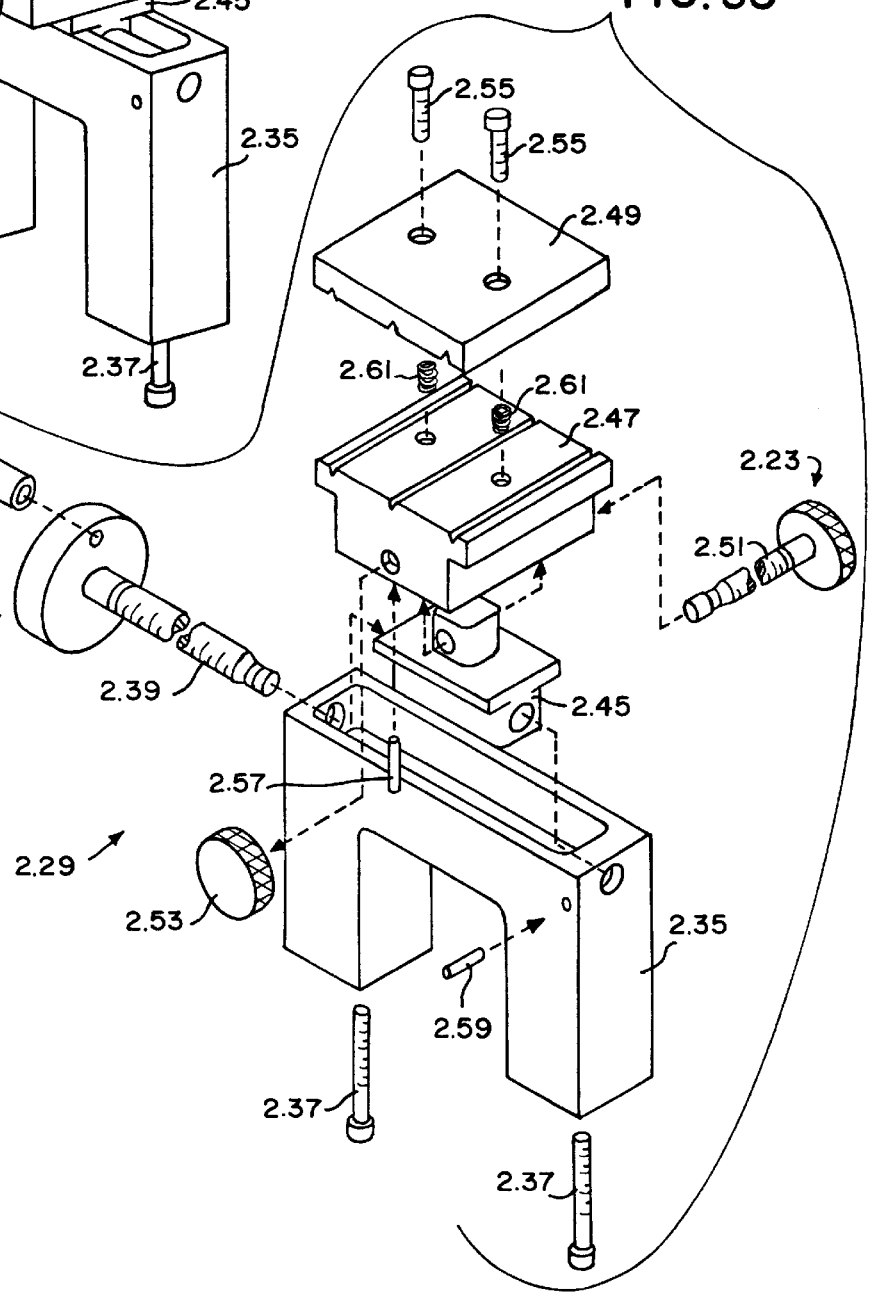

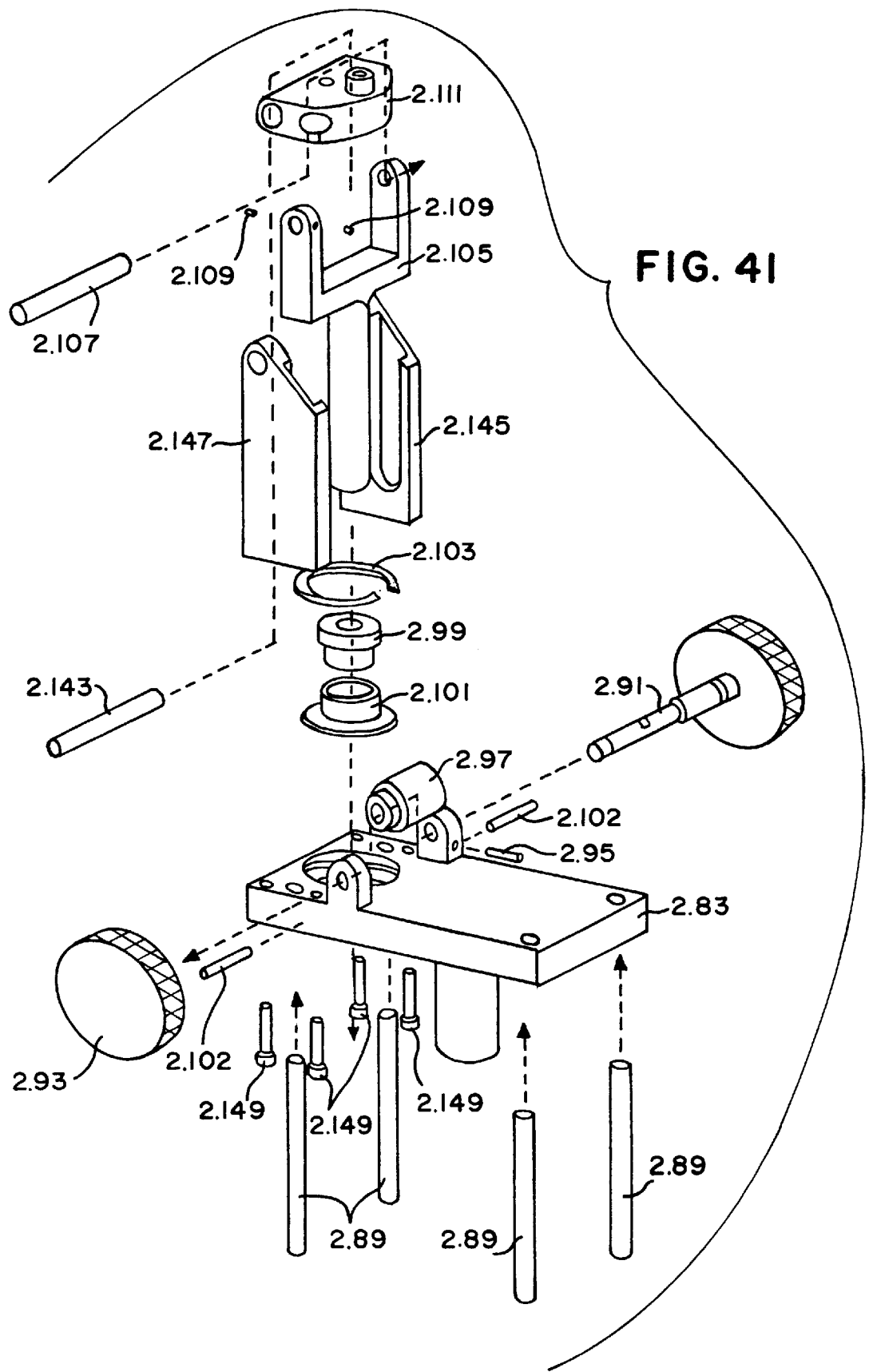

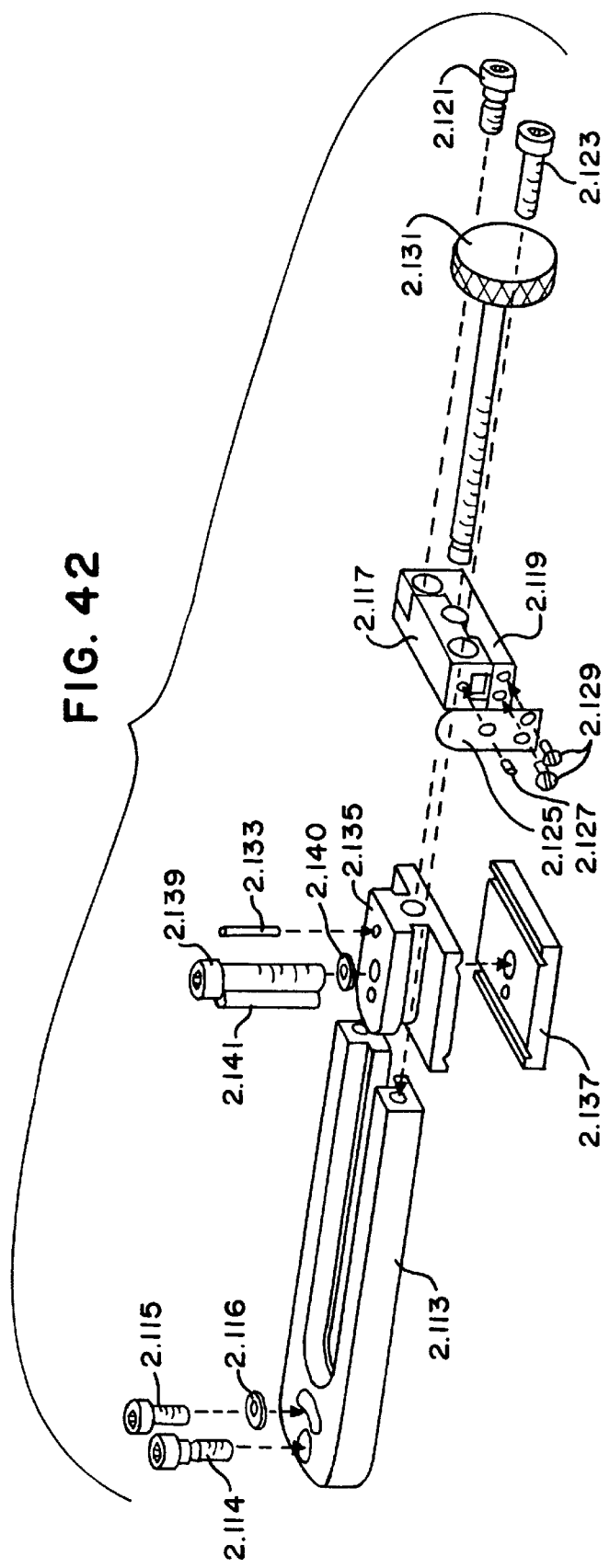

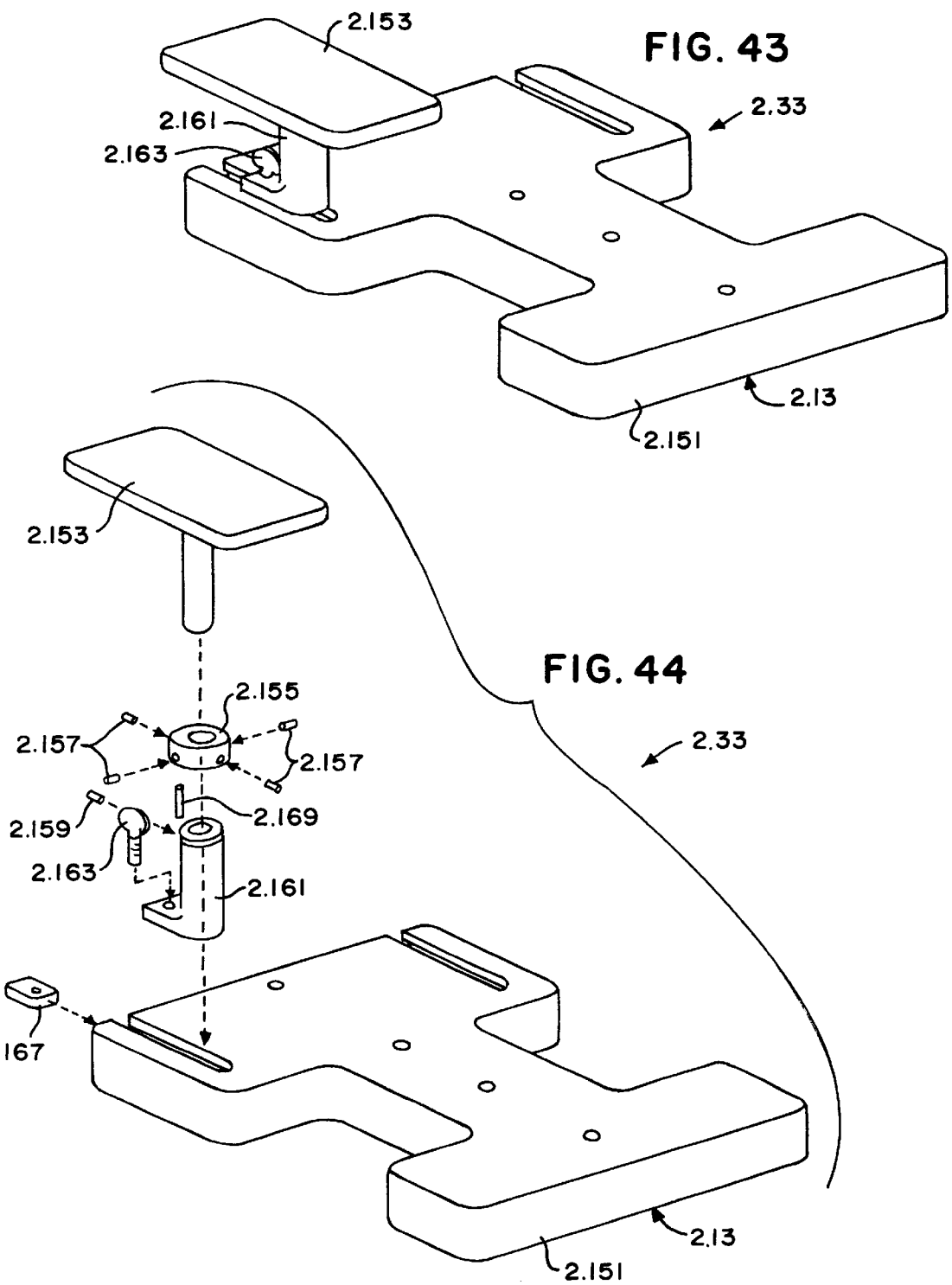

EXTERNAL FIXATION SYSTEM AND METHOD

BACKGROUND OF THE INVENTION

1. Field of the Invention

The present invention relates, in general, to a system and method used for the reduction, manipulation, and fixation of Colles' type distal radial fractures and the like.

2. Information Disclosure Statement

A preliminary patentability search produced the following patents which appear to be relevant to the present invention:

Canadell et al., U.S. Pat. No. 5,207,676, issued May 4, 1993, which discloses an external fixator with controllable damping.

Agee et al., U.S. Pat. No. 4,922,896, issued May 8, 1990, which discloses a Colles' fracture splint.

Jonsson et al., U.S. Pat. No. 4,919,119, issued Apr. 24, 1990, which discloses an external dynamic bone fixation device.

Fietti, U.S. Pat. No. 4,782,842, issued Nov. 8, 1988, which discloses an arcuate fixator for use in setting of fractured wrist or other wrist disorders.

Clyburn, U.S. Pat. No. 4,628,919, issued Dec. 16, 1986, which discloses a dynamic external fixator and method of use.

Agee et al., U.S. Pat. No. 4,611,586, issued Sep. 16, 1986, which discloses an articulated Colles' fracture splint.

Brumfield, U.S. Pat. No. 4,554,915, issued Nov. 26, 1985, which discloses a bone fixation frame.

Carrel, U.S. Pat. No. 4,409,970, issued Oct. 18, 1983, which discloses an apparatus and method for treatment of comminuted Colles' fractures.

Teague, PCT Publication No. WO 82/02830, published Sep. 2, 1982, which discloses a Colles fracture fixture device.

Chiquet, U.S. Pat. No. 4,273,116, issued Jun. 16, 1981, which discloses a device for external fixation of bone fragments.

Mraz, U.S. Pat. No. 2,333,033, issued Oct. 26, 1943, which discloses a bone splint.

Wilcox, U.S. Pat. No. 2,204,266, issued Jun. 11, 1940, which discloses a fracture reduction apparatus.

Anderson, U.S. Pat. No. 2,080,802, issued May 18, 1937, which discloses an anatomic splint.

Nothing in the known prior art discloses or suggests the present invention. Thus, nothing in the known prior art discloses or suggests an external Colles' type fracture fixator which provides pivotal adjustment about a first axis independently of any other movement thereof, pivotal adjustment about a second axis independently of any other movement thereof, pivotal adjustment about a third axis independently of any other movement thereof, translational adjustment along the first axis independently of any other movement thereof, and translational adjustment along the second axis independently of any other movement thereof. Likewise, nothing in the known prior art discloses or suggests an external alignment table which allows translational adjustment along a first axis independently of any other movement thereof, translational adjustment along a second axis independently of any other movement thereof, translational adjustment along a third axis independently of any other movement thereof, pivotal adjustment about the second axis independently of any other movement thereof, and pivotal adjustment about the third axis independently of any other movement thereof. Further, nothing in the known prior art discloses or suggests a method of externally manipulating, reducing, and stabilizing a fracture using such an external fixation alignment table and external fixator.

BRIEF SUMMARY OF THE INVENTION

The present invention provides a system and method for externally manipulating, reducing, and stabilizing a Colles' type distal radial fracture. A basic concept of the present invention is to provide an external fixation alignment table and method that allows translation adjustment of bone elements along three axes and pivotal adjustment of bone elements about two axes independently of one another. Another basic concept of the present invention is to provide an external fixator and method that provides pivotal adjustment about three axes and translational adjustment along two axes independently of one another.

The external fixator of the present invention comprises, in general, a first body member fixedly attachable to a first bone element; a second body member joined to the first body member and fixedly attachable to a second bone element; a first pivot allowing one of the body members to pivot relative to the other body member about a first axis independently of any other movement thereof; a second pivot allowing one of the body members to pivot relative to the other body member about a second axis independently of any other movement thereof; a third pivot allowing one of the body members to pivot relative to the other body member about a third axis independently of any other movement thereof; a first slide allowing one of the body members to translate relative to the other body member along the first axis independently of any other movement thereof; and a second slide allowing one of the body members to translate relative to the other body member along the second axis independently of any other movement thereof.

The external fixation alignment table of the present invention comprises, in general, a base; a first body member mounted to the base and fixedly attachable to a first bone element; a second body member mounted to the base and fixedly attachable to a second bone element; a first slide allowing one of the body members to translate relative to the other body member along a first axis independently of any other movement thereof; a second slide allowing one of the body members to translate relative to the other body member along a second axis independently of any other movement thereof; a third slide allowing one of the body members to translate relative to the other body member along a third axis independently of any other movement thereof; a first pivot allowing one of the body members to pivot relative to the other body member about the second axis independently of any other movement thereof; and a second pivot allowing one of the body members to pivot relative to the other body member about the third axis independently of any other movement thereof.

The method of externally manipulating, reducing, and stabilizing a fracture of the present invention comprises, in general, the steps of securing bone pins to first and second bone elements on opposite sides of a joint; providing an external fixation alignment table as taught by the present invention; attaching the first body member of the alignment table to the bone pins secured to the first bone member; attaching the second body member of the alignment table to the bone pins secured to the second bone member; then independently adjusting the first, second and third slides, and the first and second pivots of the alignment table to manipulate and reduce the fracture; providing an external fixator as taught by the present invention; then independently adjusting the first, second and third pivots, and the first and second slides of the fixator to position the first and second body members of the fixator in position to engage the bone pins secured to the first and second bone elements; then attaching the first and second body members of the fixator to the bone pins secured to the first and second bone elements; and then removing the alignment table from the first and second bone elements, leaving the fracture secured by the fixator.

One object of the present invention is to provide an external fixator which is modular, freely adjustable and dynamic.

Another object of the present invention is to provide such a fixator specifically designed for the treatment of traction of the distal radius and of long bones but applicable to other joints of the human body.

Another object of the present invention is to provide such a fixator that allows for adaptability and adjustability and ease of application.

Another object of the present invention is to provide such a fixator specifically designed for use in stabilizing Colles' type distal radial fractures.

Another object of the present invention is to provide such a fixator that is substantially radiolucent so as not to preclude acquisition of true medial/lateral radiographs of the distal radial fracture site while the fixator is in place.

Another object of the present invention is to provide such a fixator that can be used in either static mode or with controlled variable dynamic flexion/extension.

Another object of the present invention is to provide such a fixator that is adjustable in five independent planes of motion: 1) flexion/extension, 2) radial/ulnar deviation, 3) pronation/supination, 4) dorsal/volar translation, 5) proximal/distal translation.

Another object of the present invention is to provide such a fixator that is fabricated from a radiolucent polymer material with a rectangular "window" for radiographic visualization of the fractured distal radius in the medial/lateral plane.

Another object of the present invention is to provide a mechanical alignment table functioning through bone pins used for the multiplanar reduction of fractures of bones, and that is capable of distal radial fracture reduction by applying traction to the ligaments of a joint capsule, producing ligamentotaxis.

Another object of the present invention is to provide such an alignment table for use to externally align and reduce Colles' type distal radial fractures.

Another object of the present invention is to provide such an alignment table that can be used to position the hand in the desired amount of flexion or extension, radial-ulnar deviation, dorsal-volar translation.

Another object of the present invention is to provide such an alignment table that can be used to rotate a patient's wrist to position the longitudinal axis of the patient's hand out of alignment or plane with the longitudinal axis of the patient's forearm, and to apply traction to the patient's wrist through the distal radius and the second metacarpus, etc., along both the longitudinal axis of the patient's forearm and the longitudinal axis of the patient's hand.

Another object of the present invention is to provide such an alignment table that is used in conjunction with an external fixator to reduce and stabilize a Colles' type fracture.

BRIEF DESCRIPTION OF THE SEVERAL VIEWS OF THE DRAWINGS

FIG. 3 is a somewhat diagrammatic side elevational view of the external fixator of the present invention with portions thereof broken away for clarity, in combination with a plurality of half pins and with a portion of a distal radius having a Colles' type fracture shown in broken lines.

FIG. 4 is a somewhat diagrammatic sectional view of a portion of the external fixator of FIG. 3 but showing various parts thereof in moved positions, either in solid lines or in broken lines.

FIG. 5 is a somewhat diagrammatic top plan view of a portion of the external fixator of FIG. 3 but showing various parts thereof in moved positions, either in solid lines or in broken lines.

FIG. 6 is a somewhat diagrammatic end elevational view of the external fixator of FIG. 3.

FIG. 7 is a somewhat diagrammatic end elevational view similar to FIG. 6 but showing various parts thereof in moved positions.

FIG. 8 is a somewhat diagrammatic end elevational view similar to FIGS. 6 and 7 but showing various parts thereof in moved positions.

FIG. 37 is a somewhat diagrammatic perspective view of the radial subassembly of the external fixation alignment table of the present invention.

FIG. 38 is a somewhat diagrammatic exploded perspective view of the radial subassembly of the external fixation alignment table of the present invention.

FIG. 41 is a somewhat diagrammatic exploded perspective view of a second part of the metacarpal subassembly of the external fixation alignment table of the present invention.

FIG. 42 is a somewhat diagrammatic exploded perspective view of a third part of the metacarpal subassembly of the external fixation alignment table of the present invention.

FIG. 43 is a somewhat diagrammatic perspective view of the armrest and baseplate subassembly of the external fixation alignment table of the present invention.

FIG. 44 is a somewhat diagrammatic exploded perspective view of the armrest and baseplate subassembly of the external fixation alignment table of the present invention.

DETAILED DESCRIPTION OF THE INVENTION

The preferred embodiment of the external fixation system of the present invention is intended to be used as an external manipulator and stabilizer for the purpose of promoting healing of Colles' type distal radial fractures in skeletally mature individuals, and includes four basic parts: (1) an alignment/reduction table, (2) an external fixator, (3) a series of threaded half pins, and (4) ancillary tools.

Figure 1:
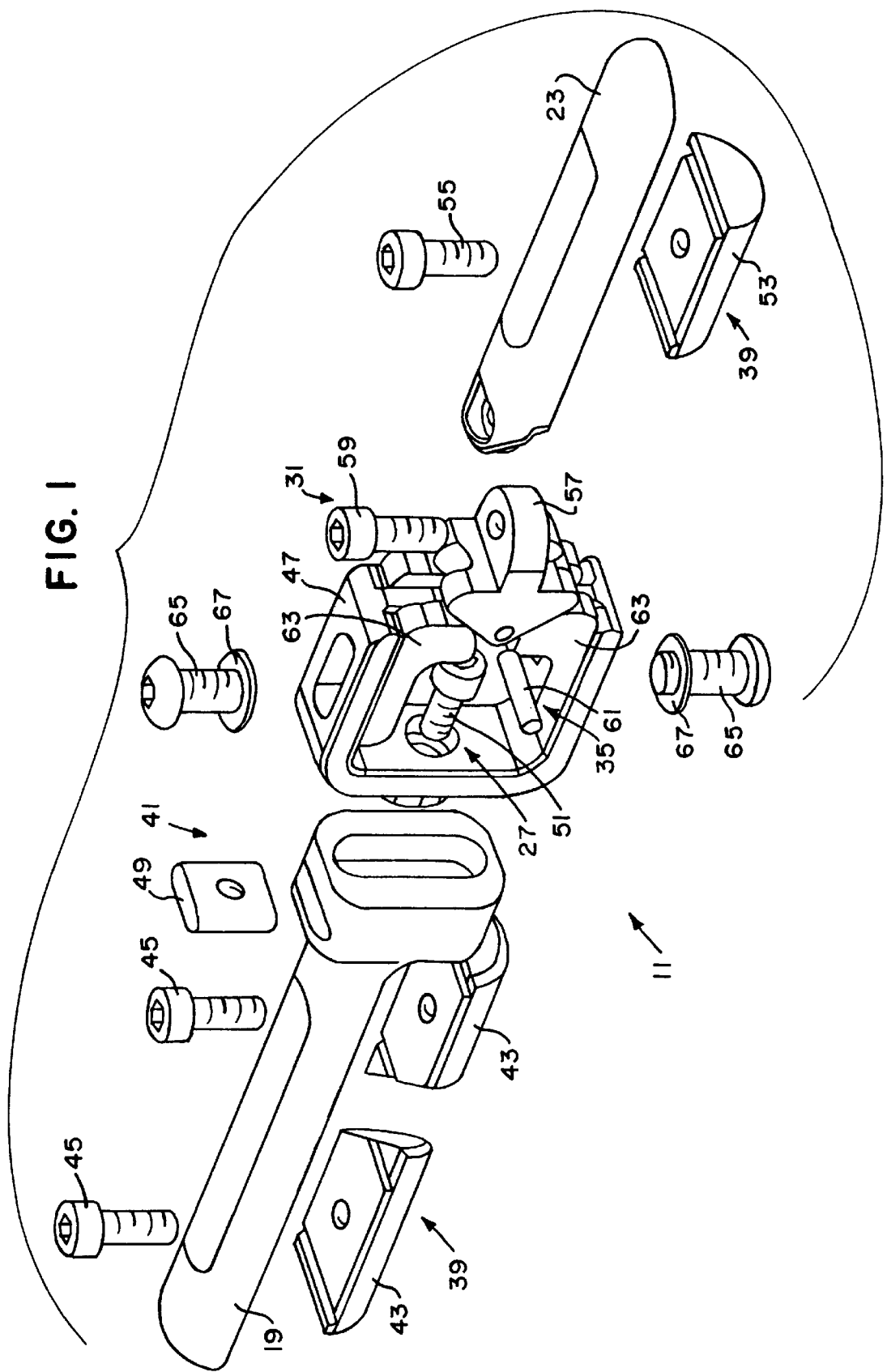
FIG. 1 is a somewhat diagrammatic exploded perspective view of the external fixator of the present invention.
Figure 2:
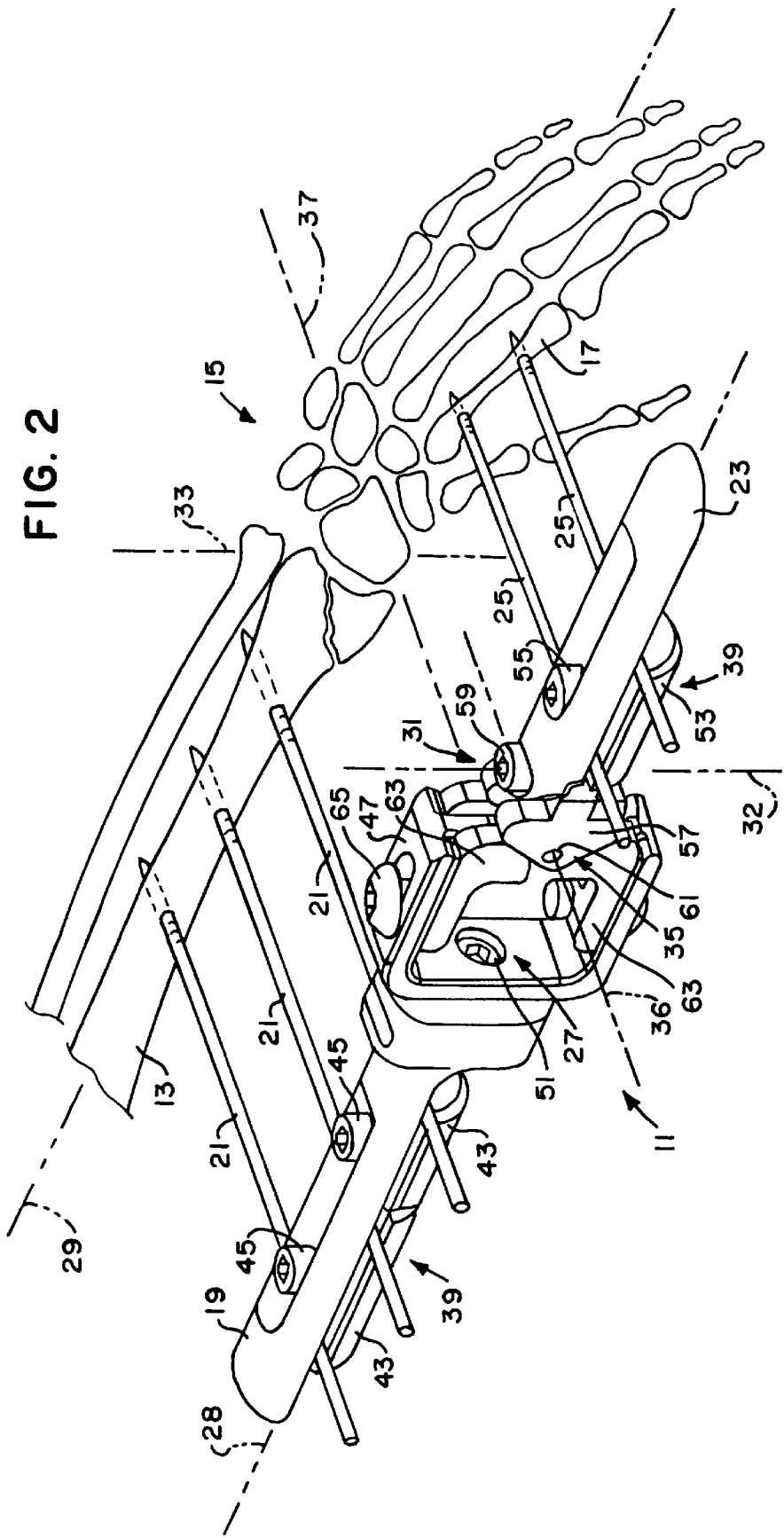
FIG. 2 is a somewhat diagrammatic perspective view of the external fixator of the present invention shown in combination with a plurality of half pins securing a Colles' type fracture of a distal radius.
Figure 9:
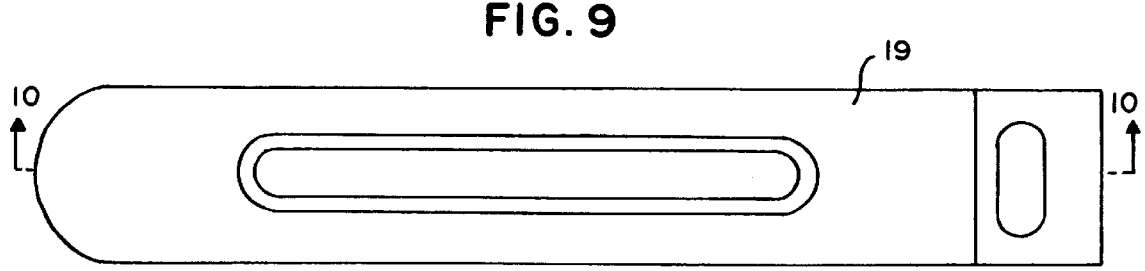
FIG. 9 is a top plan view of a radial track of the preferred embodiment of the external fixator of the present invention.
Figure 10:
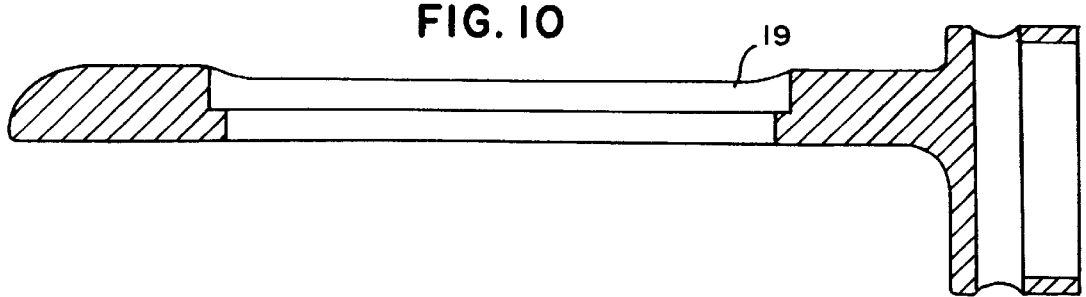
FIG. 10 is a sectional view as taken on line 10—10 of FIG. 9.
Figure 11:
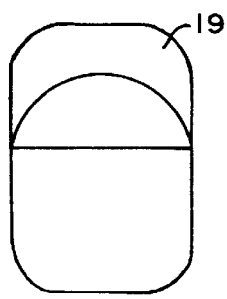
FIG. 11 is a first end elevational view of the radial track of FIG. 9.
Figure 12:
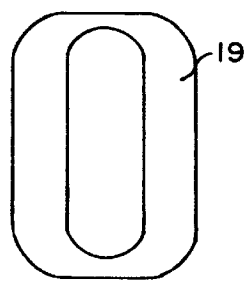
FIG. 12 is a second end elevational view of the radial track of FIG. 9.
Figure 13:
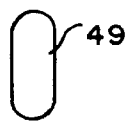
FIG. 13 is a top plan view of a radial T-nut of the preferred embodiment of the external fixator of the present invention.
Figure 14:
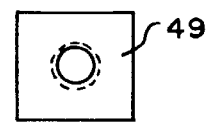
FIG. 14 is a face elevational view of the radial T-nut of FIG. 13.
Figure 15:
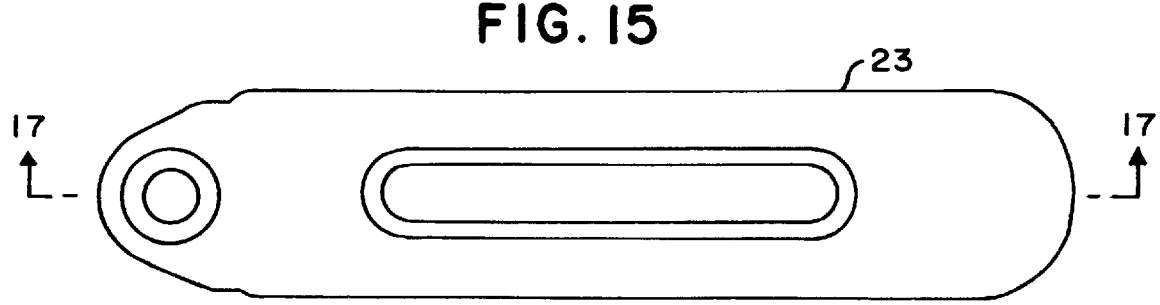
FIG. 15 is a top plan view of a metacarpal track of the preferred embodiment of the external fixator of the present invention.
Figure 16:
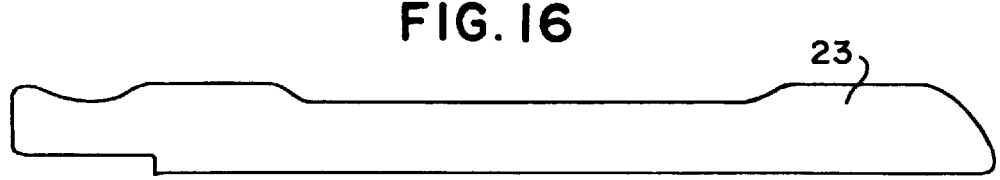
FIG. 16 is a side elevational view of the metacarpal track of FIG. 15.
Figure 17:
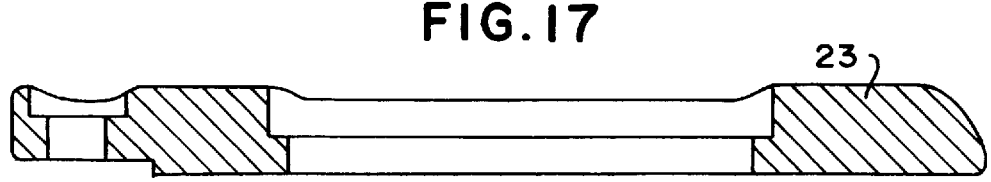
FIG. 17 is a sectional view as taken on line 17—17 of FIG. 15.
Figure 18:
FIG. 18 is an end elevational view of the metacarpal track of FIG. 15.
Figure 19:
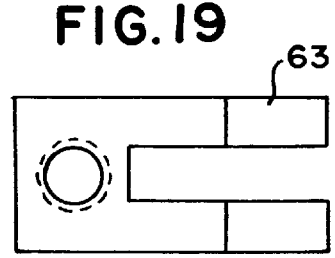
FIG. 19 is a top plan view of a flexion/extension stop of the preferred embodiment of the external fixator of the present invention.
Figure 20:
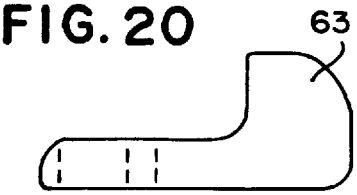
FIG. 20 is a side elevational view of the flexion/extension stop of FIG. 19.
Figure 21:
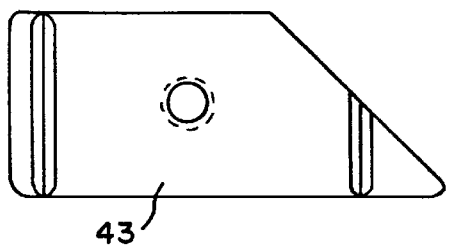
FIG. 21 is a top plan view of a radial proximal clamp of the preferred embodiment of the external fixator of the present invention.
Figure 22:
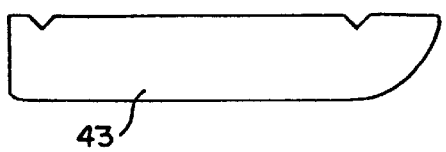
FIG. 22 is a side elevational view of the radial proximal clamp of FIG. 21.
Figure 23:
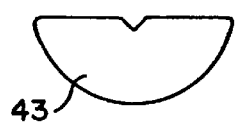
FIG. 23 is an end elevational view of the radial proximal clamp of FIG. 21.
Figure 24:
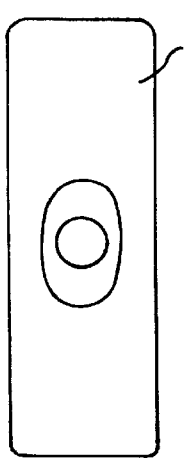
FIG. 24 is a first end elevational view of a central block of the preferred embodiment of the external fixator of the present invention.
Figure 25:
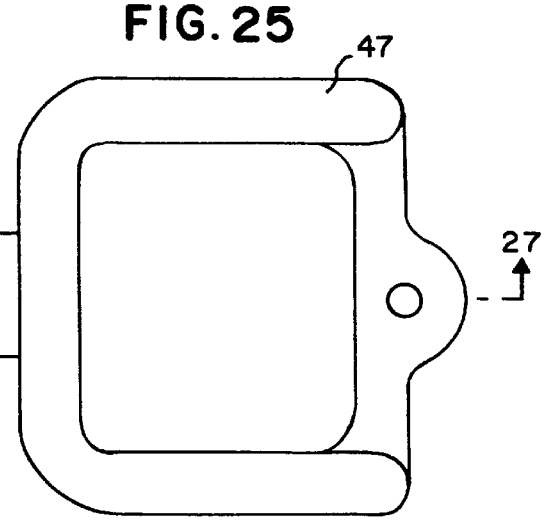
FIG. 25 is a side elevational view of the central block of FIG. 24.
Figure 26:
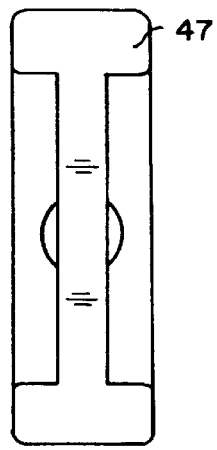
FIG. 26 is a second end elevational view of the central block of FIG. 24.
Figure 27:
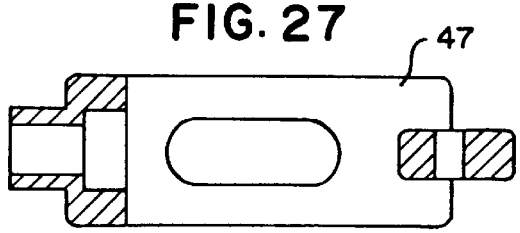
FIG. 27 is a sectional view as taken on line 27—27 of FIG. 25.
Figure 28:
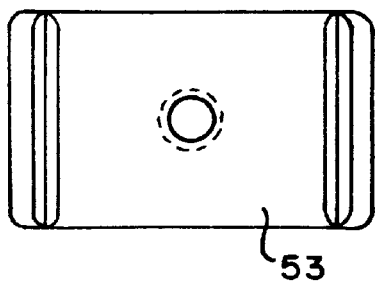
FIG. 28 is a top plan view of a metacarpal clamp of the preferred embodiment of the external fixator of the present invention.
Figure 29:
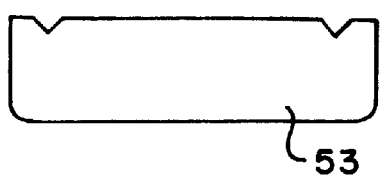
FIG. 29 is a side elevational view of the metacarpal clamp of FIG. 28.
Figure 30:
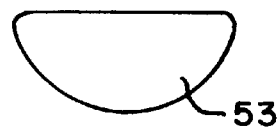
FIG. 30 is an end elevational view of the metacarpal clamp of FIG. 28.
Figure 31:
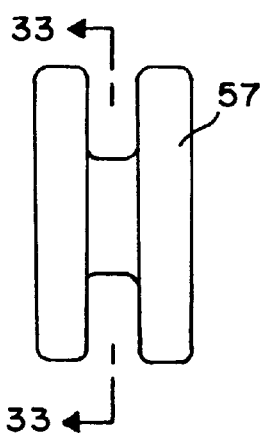
FIG. 31 is a end elevational view of a central hinge of the preferred embodiment of the external fixator of the present invention.
Figure 32:
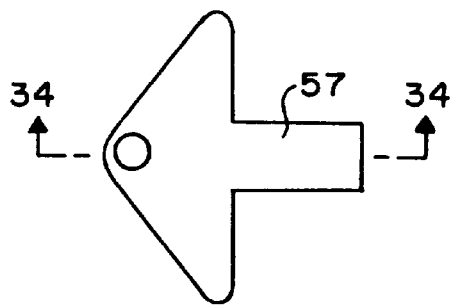
FIG. 32 is a side elevational view of the central hinge of FIG. 31.
Figure 33:
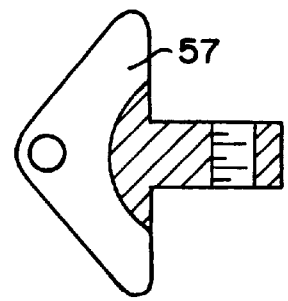
FIG. 33 is a sectional view as taken on line 33—33 of FIG. 31.
Figure 34:
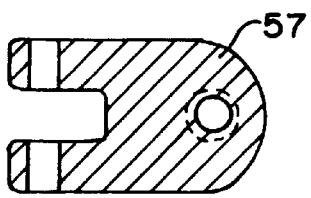
FIG. 34 is a sectional view as taken on line 34—34 of FIG. 32.
Figure 35:
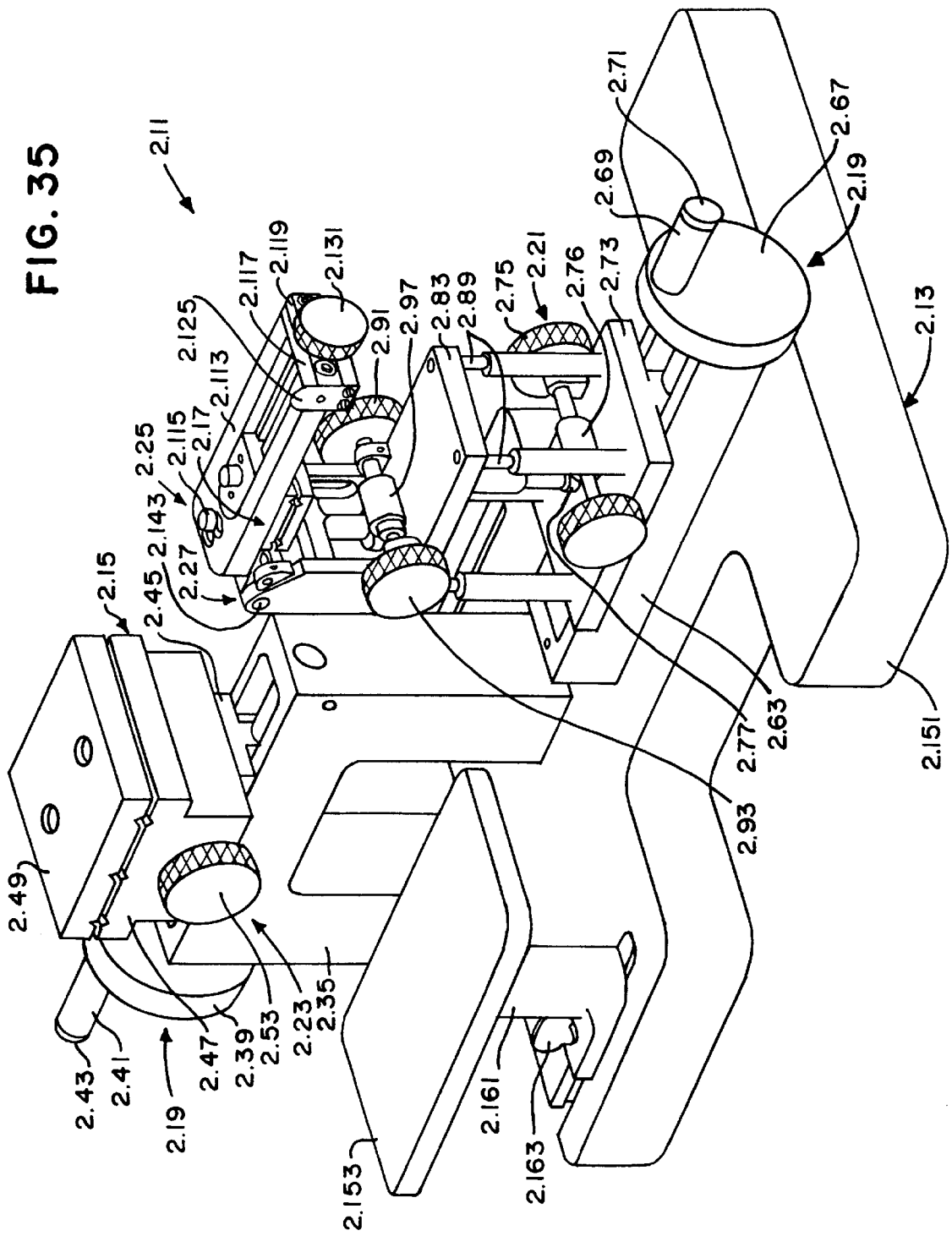
FIG. 35 is a somewhat diagrammatic perspective view of the external fixation alignment table of the present invention, with the armrest and baseplate subassembly thereof shown in a position to support a patient's right forearm.

A preferred embodiment of the external fixator of the present invention is shown in FIGS. 1–34, and identified by the numeral 11. The preferred embodiment of the external fixator 11 will be a single-use disposable device used to provide secure fixation of Colles' type distal radial fractures to promote healing, for use as either a static rigid body type fixator or as a dynamic type fixator. Thus, the external fixator 11 is used to secure a Colles' type fracture involving a first bone element, e.g., a radius 13, on a first side of a joint, e.g., on the proximal side of a wrist joint 15, and a second bone element, e.g., a second metacarpus 17, on a second side of the joint, e.g., on the distal side of the wrist joint 15 (see, in general, FIG. 2).

The external fixator 11 includes a first body member or radial track 19 fixedly attachable to the first bone element, e.g., the radius 13, by way of a plurality of bone fixation members such as threaded half pins 21 or the like.

The external fixator 11 includes a second body member or metacarpal track 23 joined to the first body member or radial track 19 and fixedly attachable to the second bone element, e.g., the second metacarpus 17, by way of a plurality of bone fixation members such as threaded half pins 25 or the like.

Thus, the external fixator 11 is preferably secured to the wrist by five partially threaded half pins 21, 25. Two half pins 25 are preferably used to secure the fixator 11 to the second metacarpus 17 and three half pins 21 are preferably used to secure the fixator 11 to the distal radius 13.

The first and second body members, i.e., the radial track 19 and metacarpal track 23, are joined to one another and to the bone fixation members, i.e., to the half pins 21, 25, by structure specifically designed to allow relative movement thereof in five independently adjustable axes of motion. The axes are as follows: 1) flexion/extension, 2) radial/ulnar deviation, 3) pronation/supination, 4) dorsal/volar translation, and 5) proximal/distal translation. More specifically, the external fixator 11 includes a first pivot 27 allowing one of the body members 19, 23 to pivot relative to the other body member 19, 23 about a first axis 28 (i.e., an axis parallel or substantially parallel to the longitudinal axis 29 of the forearm or radius 13) independently of any other movement thereof, thereby providing pronation/supination; a second pivot 31 allowing one of the body members 19, 23 to pivot relative to the other body member 19, 23 about a second axis 32 (i.e., an axis parallel or substantially parallel to the normally vertical axis 33 through the wrist joint 15 substantially perpendicular to the first axis 28) independently of any other movement thereof, thereby providing radial/ulnar deviation; a third pivot 35 allowing one of the body members 19, 23 to pivot relative to the other body member 19, 23 about a third axis 36 (i.e., an axis parallel or substantially parallel to, and coaxial with, the normally horizontal or transverse axis 37 through the wrist joint 15 substantially perpendicular to the first and second axes 28, 32) independently of any other movement thereof, thereby providing flexion/extension; a first slide 39 allowing one of the body members 19, 23 to translate relative to the other body member 19, 23 along the first axis 28 independently of any other movement thereof, thereby providing proximal/distal translation; and a second slide 41 allowing one of the body members 19, 23 to translate relative to the other body member 19, 23 along the second axis 32 independently of any other movement thereof, thereby providing dorsal/volar translation.

The external fixator 11 is preferably designed to be capable of the following ranges of motion: +/–50° flexion/extension range of motion (i.e., rotation about the third axis 36); +/–30° radial/ulnar deviation range of motion (i.e., rotation about the second axis 32); +/–10° pronation/supination range of motion (i.e., rotation about the first axis 28); +/–0.5 inch (1.27 centimeters) dorsal/volar translation range of motion (i.e., translation along the second axis 32); and 0.75 inch (1.905 centimeters) total proximal/distal translation range of motion (i.e., translation along the first axis 28).

The external fixator 11 preferably includes at least one and preferably two radial proximal clamps 43 and radial clamp screws 45 for coacting with the radial track 19 to securely clamp the half pins 21 therebetween, a central block 47, a radial T-nut 49 and a central block clamp screw 51 for coacting to secure the central block 47 to the radial track 19, at least one metacarpal clamp 53 and metacarpal clamp screw 55 for coacting with the metacarpal track 23 to securely clamp the half pins 25 therebetween, a central hinge 57, a central hinge clamp screw 59 for clamping the metacarpal track 23 and the central hinge 57 together, and a hinge pin 61 for attaching the central block 47 and central hinge 57 together. The first pivot 27 is defined or formed by the central block clamp screw 51. The second pivot 31 is defined or formed by the central hinge clamp screw 59. The third pivot 35 is defined or formed by the hinge pin 61. The first slide 39 is defined or formed by the combined radial track 19, radial proximal clamps 43, and radial clamp screws 45, and/or the combined metacarpal track 23, metacarpal clamp 53, and metacarpal clamp screw 55. In addition, the external fixator 11 preferably includes at least one and preferably two flexion/extension stops 63 and flexion/extension stop clamp screws 65 for coacting to limit the rotation of the body members 19, 23 about the third axis 36. Internal tooth lock washers 67 may be provided for the flexion/extension stop clamp screws 65. Of the axes of motion of the fixator 11, the flexion/extension axis can be used in either a static or a dynamic mode. In the static mode the external fixator 11 acts as a rigid body. In dynamic mode, the amount of flexion and/or extension allowed is user set by adjusting the flexion/extension stops 63 to the desired positions.

The radial track 19, metacarpal track 23, radial proximal clamps 43, central block 47, radial T-nut 49, metacarpal clamp 53, central hinge 57, and flexion/extension stops 63 of the external fixator 11 are preferably injection molded and otherwise fabricated out of a radiolucent polymer material or plastic such as 33% glass fiber reinforced PPA resin conforming to ASTM D 5336. The radial clamp screws 45, central block clamp screw 51, metacarpal clamp screw 55, central hinge clamp screw 59, hinge pin 61, and flexion/extension stop clamp screws 65 are preferably machined or otherwise fabricated from stainless steel such as cold-worked 303 stainless steel. The external fixator 11 is preferably a "one size fits all" design since its effective length and attachment positions are user adjustable.

A preferred embodiment of the external fixation alignment table of the present invention is shown in FIGS. 35–44, and identified by the numeral 2.11. The preferred embodiment of the alignment table 2.11 is especially designed as a reusable multipurpose device designed to reduce distal radial fracture fragments, move the hand into the desired position, and hold it in place during attachment of the external fixator device 11. The preferred embodiment of the alignment table 2.11 will be a large platform based device that is fully adjustable in all of the planes of motion of the wrist joint, and will have the ability to manipulate the hand so as to correct malalignment due to displacement as a result of the fracture. Thus, the alignment table 2.11 can be used to manipulate and reduce a Colles' type fracture involving a first bone element, i.e., the radius 13, on a first side of a joint, i.e., on the proximal side of the wrist joint 15, and a second bone element, i.e., the second metacarpal 17, on a second side of the joint, i.e., on the distal side of the wrist joint 15. The alignment table 2.11 is capable of attaching to the threaded half pins 21, 25, manipulating the patient's hand into a desired position and orientation, and applying a traction force to the wrist joint to produce tension in the ligamentous structures of the joint capsule.

The alignment table 2.11 includes a base 2.13; a first body member 2.15 mounted to the base 2.13 and fixedly attachable to a first bone element, e.g., the radius 13, by way of a plurality of bone fixation members such as the threaded half pins 21 or the like; and a second body member 2.17 mounted to the base 2.13 and fixedly attachable to a second bone element, e.g., the second metacarpus 17, by way of a plurality of bone fixation members such as the threaded half pins 25 or the like.

The first and second body members 2.15, 2.17 are joined to the base 2.13, to one another, and to the bone fixation members, i.e., to the half pins 21, 25, by structure specifically designed to allow relative movement thereof in five independently controllable planes of motion. The planes of motion are as follows: 1) flexion/extension, 2) radial/ulnar deviation, 3) dorsal/palmar translation, 4) medial/lateral translation, and 5) proximal/distal translation. More specifically, the alignment table 2.11 includes a first slide 2.19 allowing one of the body members 2.15, 2.17 to translate relative to the other body member 2.15, 2.17 along a first axis 2.20 (i.e., an axis parallel or substantially parallel to the longitudinal axis 29 of the radius 13) independently of any other movement thereof; a second slide 2.21 allowing one of the body members 2.15, 2.17 to translate relative to the other body member 2.15, 2.17 along a second axis 2.22 (i.e., an axis parallel or substantially parallel to the normally vertical axis 33 through the wrist joint 15 substantially perpendicular to the first axis 2.20) independently of any other movement thereof; a third slide 2.23 allowing one of the body members 2.15, 2.17 to translate relative to the other body member 2.15, 2.17 along a third axis 2.22 (i.e., an axis parallel or substantially parallel to the normally horizontal or transverse axis 37 through the wrist joint 15 substantially perpendicular to the first and second axes 2.20, 2.22) independently of any other movement thereof; a first pivot 2.25 allowing one of the body members 2.15, 2.17 to pivot relative to the other body member 2.15, 2.17 about the second axis 2.22 independently of any other movement thereof; and a second pivot 2.27 allowing one of the body members 2.15, 2.17 to pivot relative to the other body member 2.15, 2.17 about the third axis 2.24 independently of any other movement thereof. The alignment table 2.11 preferably includes appropriately marked hand cranks or dials to allow easy individual manual adjustment of the body members 2.15, 2.17 about and along the several axes until the desired amount of adjustment has be achieved.

The preferred embodiment of the alignment table 2.11 can generally be divided into three basic components or constructs: a radial subassembly 2.29, a metacarpal subassembly 2.31, and an armrest and baseplate subassembly 2.33.

The radial subassembly 2.29 preferably forms the first body member 2.15 and includes a radial mounting base 2.35, a pair of radial mounting screws 2.37, a radial crankshaft 2.39, a radial crankshaft handle 2.41, a radial crankshaft handle screw 2.43, a radial slide 2.45, a radial pin holder bottom 2.47, a radial pin holder top 2.49, a radial pin holder shaft 2.51, a radial pin holder knob 2.53, a pair of radial pin holder clamp screws 2.55, a radial pin holder dowel 2.57, a radial base dowel 2.59, and a pair of compression springs 2.61.

The metacarpal subassembly 2.31 preferably forms the second body member 2.17 and includes a metacarpal mounting base 2.63, a pair of metacarpal mounting screws 2.65, a metacarpal crankshaft 2.67, a metacarpal crankshaft handle 2.69, a metacarpal crankshaft handle screw 2.71, a metacarpal crankshaft dowel 2.72, a metacarpal slide base 2.73, a metacarpal elevator shaft 2.75, a metacarpal elevator worm 2.76, a metacarpal elevator worm gear 2.77, a metacarpal elevator rod 2.79, a metacarpal elevator rod dowel 2.81, a metacarpal base dowel 2.82, a metacarpal adjuster base 2.83, four metacarpal adjuster base guide rods 2.89, a metacarpal inclinator shaft 2.91, a metacarpal inclinator knob 2.93, a metacarpal inclinator shaft dowel 2.95, a metacarpal inclinator worm 2.97, a metacarpal inclinator worm gear 2.99, a metacarpal inclinator worm gear holder 2.101, two metacarpal inclinator worm gear holder dowels 2.102, a metacarpal inclinator snap ring 2.103, a metacarpal inclinator rod 2.105, a metacarpal inclinator rod pin 2.107, two metacarpal inclinator rod dowels 2.109, a metacarpal inclinator base 2.111, a metacarpal rotation base 2.113, a metacarpal rotator base pivot shoulder screw 2.114, a metacarpal rotator base lock screw 2.115, a metacarpal rotator base lock screw washer 2.116, a metacarpal rotator end cap base 2.117, a metacarpal rotator end cap clamp 2.119, a metacarpal rotator end cap shoulder screws 2.121, a metacarpal rotator end cap screw 2.123, a metacarpal rotator end clamp lock plate 2.125, a metacarpal rotator end cap lock button 2.127, two metacarpal rotator end cap clamp lock screw 2.129, a metacarpal rotator crankshaft 2.131, a metacarpal rotator crankshaft dowel 2.133, a metacarpal pin holder slide 2.135, a metacarpal pin holder bottom 2.137, a metacarpal pin holder screw 2.139, a metacarpal pin holder screw washer 2.140, a split pin dowel 2.141, a metacarpal main pivot rod 2.143, a metacarpal right side slide 2.145, a metacarpal left side slide 2.147, and four side slide cap screws 2.149.

The armrest and baseplate subassembly 2.33 preferably forms the base 2.13, and includes a table baseplate 2.151, an armrest plate 2.153, an armrest adjuster knob 2.155, four split pins 2.157, a split pin 2.159, an armrest guide tube 2.161, an armrest thumb screw 2.163, an armrest slide nut 2.167, and a split pin 2.169.

Figure 36:
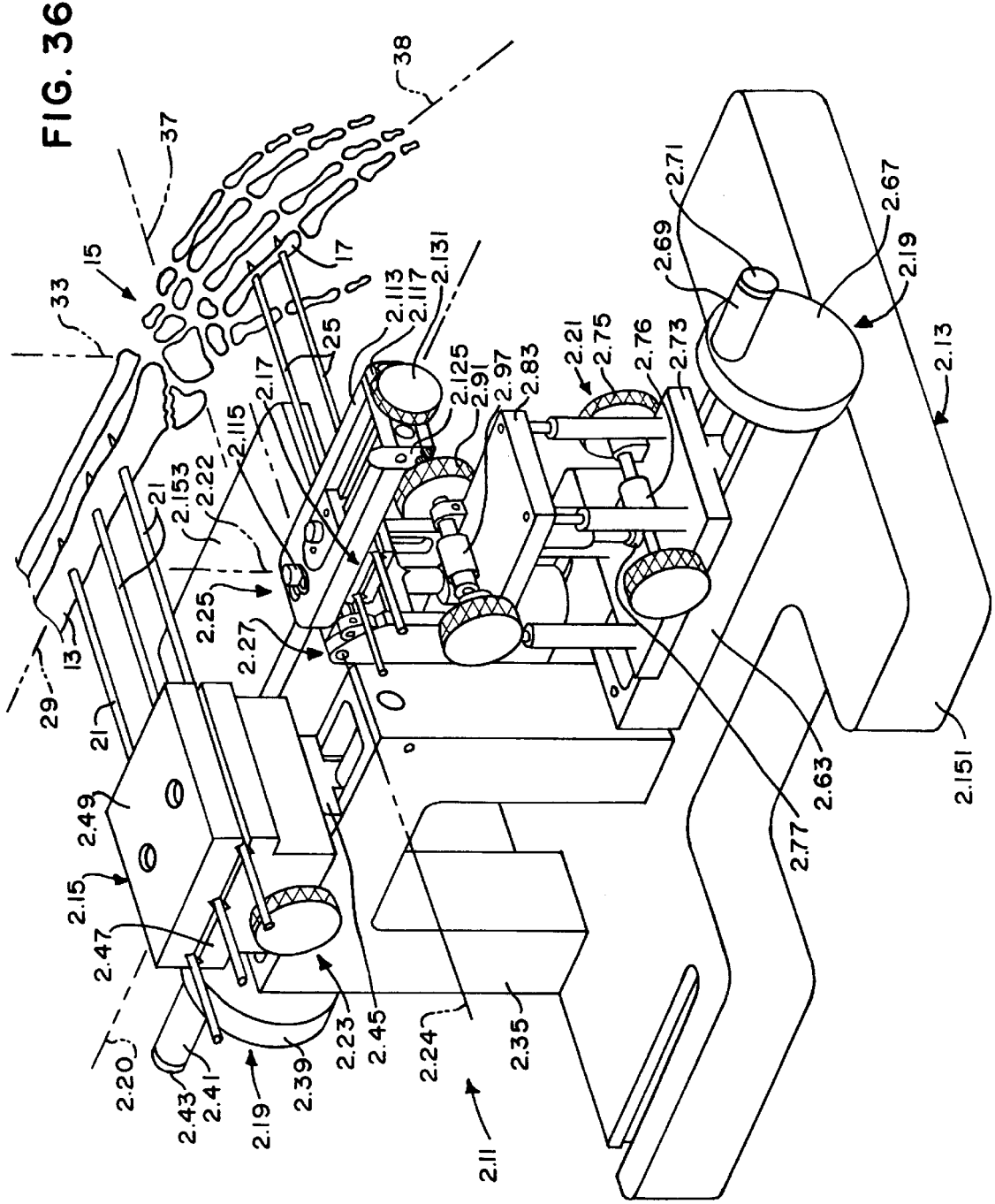
FIG. 36 is a somewhat diagrammatic perspective view of the external fixation alignment table of the present invention shown in combination with a plurality of half pins securing a Colles' type fracture of a distal radius, and with the armrest and baseplate subassembly thereof shown in a position to support a patient's left forearm.
Figure 39:
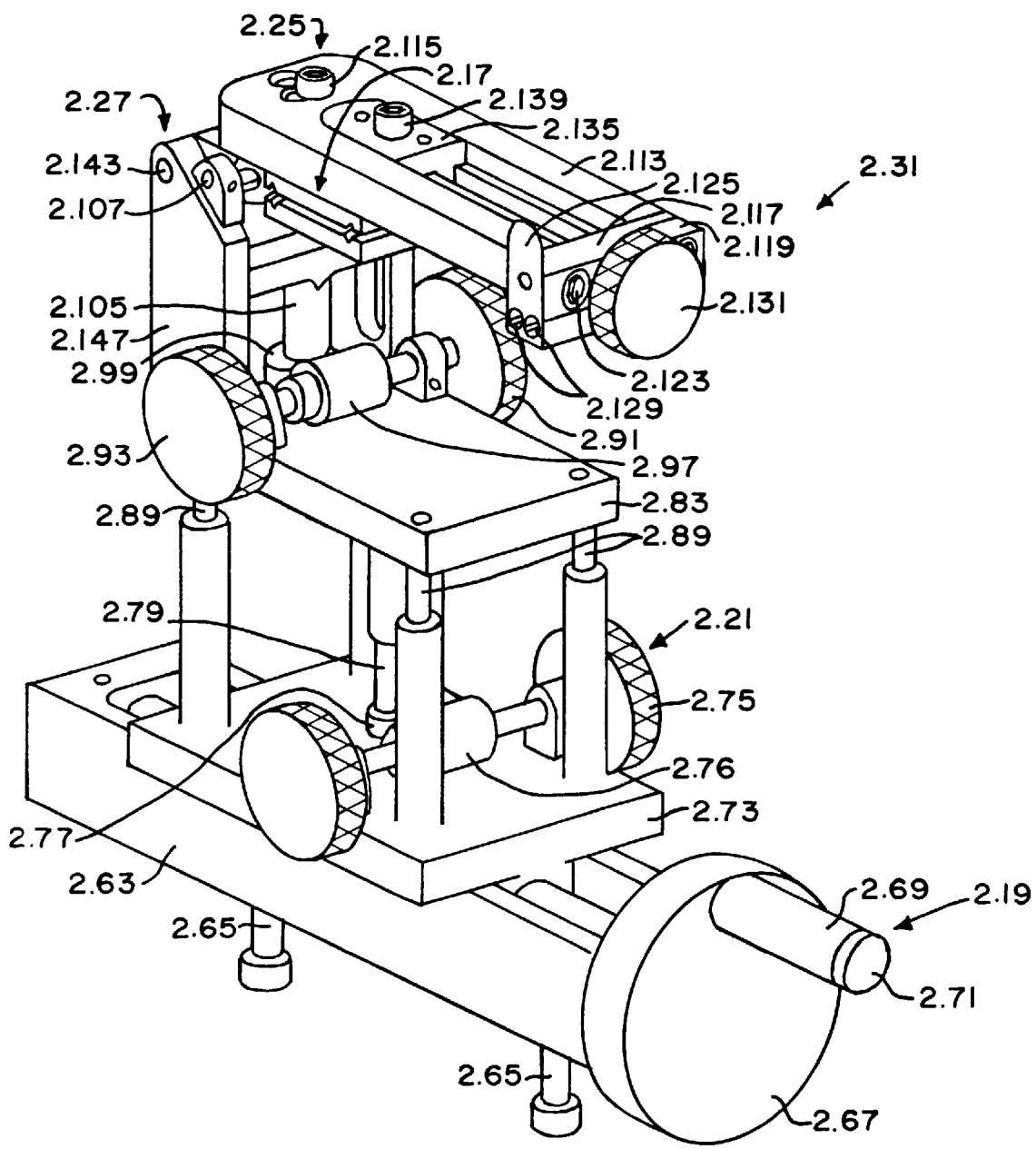
FIG. 39 is a somewhat diagrammatic perspective view of the metacarpal subassembly of the external fixation alignment table of the present invention.
Figure 40:
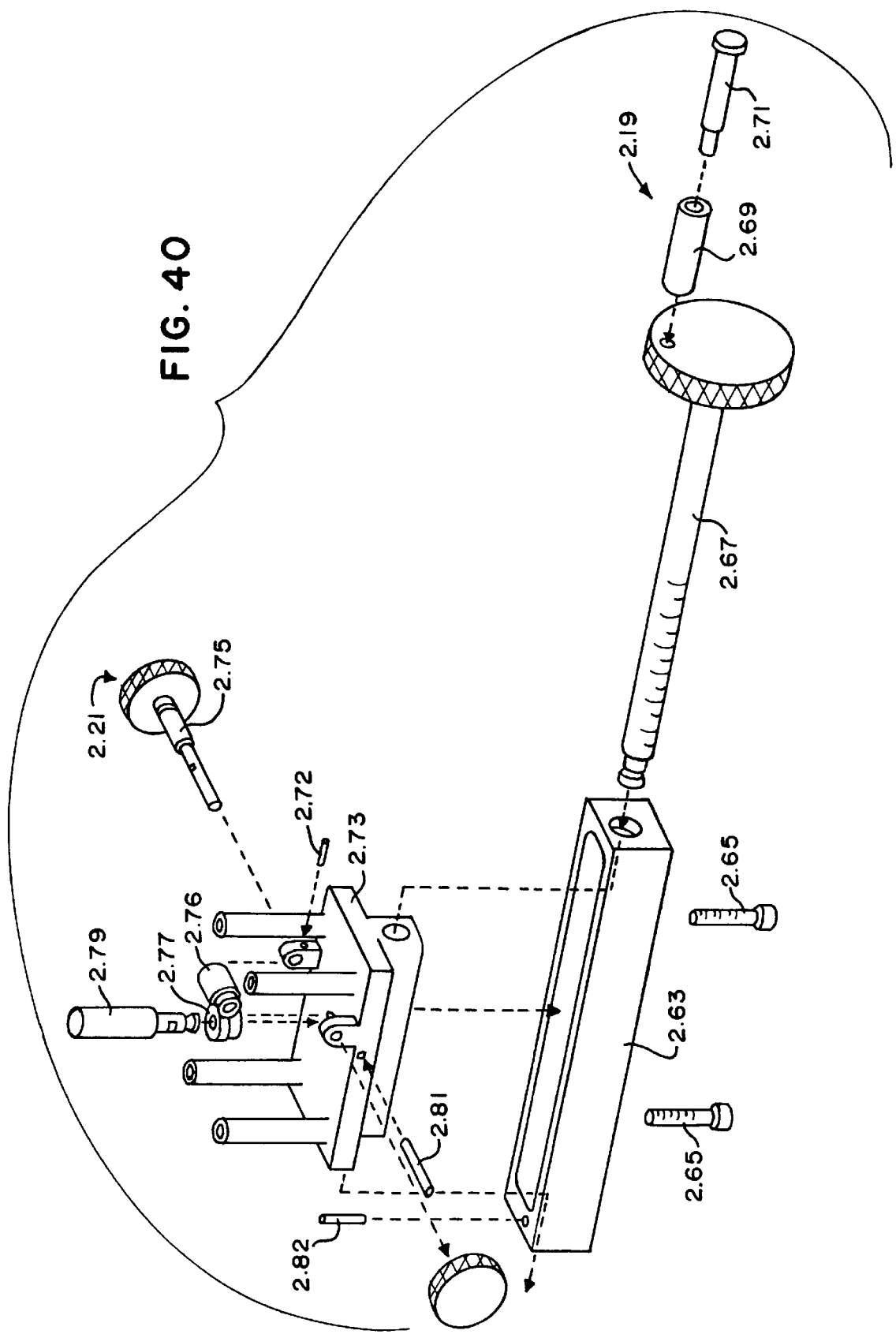
FIG. 40 is a somewhat diagrammatic exploded perspective view of a first part of the metacarpal subassembly of the external fixation alignment table of the present invention.

The first slide 2.19 is defined or formed by the combined radial crankshaft 2.39 and radial slide 2.45, etc., of the radial subassembly 2.29; and the metacarpal crankshaft 2.67 and metacarpal slide base 2.73, etc., of the metacarpal subassembly 2.31. The second slide 2.21 is defined or formed by the combined metacarpal elevator shaft 2.75, metacarpal elevator worm 2.76, metacarpal elevator worm gear 2.77, metacarpal elevator rod 2.79, etc., of the metacarpal subassembly 2.31. The third slide 2.23 is defined or formed by the combined radial slide 2.45, radial pin holder bottom 2.47, radial pin holder shaft 2.51, etc., of the radial subassembly 2.29. The first pivot 2.25 is defined or formed by the combined metacarpal inclinator base 2.111, metacarpal rotator base 2.113, metacarpal rotator base pivot shoulder screw 2.114, and the metacarpal rotator crankshaft 2.131, metacarpal pin holder slide 2.135, etc., of the metacarpal subassembly 2.31. When the alignment table 2.11 is secured to the patient's forearm and hand by way of, for example, the half pins 21, 25 as shown in FIG. 36, and when the metacarpal rotator base lock screw 2.115 is loose and the metacarpal rotator crankshaft 2.131 is rotated, the specific design of the first pivot 2.25 will cause the patient's hand to rotate about the axis 33, changing the alignment of the longitudinal axis 38 of the patient's hand relative to the longitudinal axis 29 of the patient's forearm or radius 13. When the radial crankshaft 2.39 and/or metacarpal crankshaft 2.67 are rotated, the combined radial crankshaft 2.39 and radial slide 2.45, etc., of the radial subassembly 2.29, and the metacarpal crankshaft 2.67 and metacarpal slide base 2.73, etc., of the metacarpal subassembly 2.31, will cause traction to be applied along the longitudinal axis 29 of the forearm or radius 13. However, when the metacarpal rotator base lock screw 2.115 is locked (i.e., tightened), rotation of the metacarpal rotator crankshaft 2.131 will cause translation of the metacarpal pin holder slide 2.135, etc., thereby applying traction along the longitudinal axis 38 of the patient's hand. The design of the metacarpal rotator end cap base 2.117, metacarpal rotator end cap clamp 2.119, metacarpal rotator end clamp lock plate 2.127, etc., allows the metacarpal rotator crankshaft 2.131 and associated metacarpal pin holder slide 2.135, etc., to be manually released from the metacarpal rotator base 2.113 and slide back and forth in the metacarpal rotator base 2.113 to make quick, gross adjustment of the first pivot 2.25, etc. The second pivot 2.27 is defined or formed by the combined metacarpal inclinator shaft 2.91, metacarpal inclinator worm 2.97, metacarpal inclinator worm gear 2.99, metacarpal inclinator rod 2.105, metacarpal inclinator rod pin 2.107, etc., of the metacarpal subassembly 2.31.

There will be only one size alignment/reduction table to be used with this system. The alignment table 2.11 is preferably a finished level assembly with component parts fabricated as follows: The table baseplate 2.151 is preferably fabricated from Delrin, acetal homopolymer, conforming to ASTM D 4181, POM 130. The threaded shaft components and knurled knobs are preferably fabricated from 630 stainless steel, conforming to ASTM A 564, type 630. The socket head cap screws and slotted head screws are preferably be fabricated from 303 stainless steel, conforming to ASTM A 582, type 303. The roll spring pins are preferably fabricated from 420 stainless steel, conforming to ASTM A 176, type 420. The worm gears are preferably fabricated from naval bronze conforming to Mil. Spec. QQ-B-637, alloy 464. The worms are preferably fabricated from 303 stainless steel conforming to ASTM A 582, type 303. The crankshaft handles are preferably fabricated from ULTEM 1000. The guide rods and hinge pins are preferably fabricated from 303 stainless steel conforming to ASTM A 582, type 303. The metacarpal clamp lock plate 2.125 and button 2.127 are preferably fabricated from 630 stainless steel conforming to ASTM A 564, type 630. All other structural components are preferably fabricated from aluminum alloy conforming to ASTM B 221, alloy 6061, T6511.

The ancillary tools for the system are preferably single use disposable items and preferably include a radial drill guide, a metacarpal drill guide, a ball end type hex wrench, and a set of six pin end caps. The system preferably includes a disposable blister type instrument tray to provide packaging to hold and organize the half pins 21, 25, ancillary tools, and fixator 11.

The threaded half pins 21, 25 are preferably machined or otherwise fabricated out of stainless steel such as cold-worked 316 LVM stainless steel, and are preferably provided in two sizes. The metacarpal pins 25 are preferably 2.5 millimeters in diameter and the radial pins 21 are preferably 3.0 millimeters in diameter. Both type of pins 21, 25 are preferably approximately 200 millimeters long. The initial length of the half pins 21, 25 is not critical since they will be cut to the desired length after application of the fixator 11. The threaded half pins 21, 25 are preferably used to secure the external fixator 11 to the bony structures of the forearm and hand, namely the radius 13 and second metacarpal 17, respectively. The half pins 21, 25 will be the only portion of the system to be implanted directly into the patient, and are preferably single use disposable items. The threaded half pins 21, 25 are preferably self drilling and self tapping for ease of insertion into the bony structures of the hand and forearm. The metacarpal drill guide will be one size only with bore diameters slightly larger than 2.5 mm to allow for passage of the metacarpal half pins. The metacarpal drill guide will preferably be a molded plastic part consisting of two equally spaced parallel drill guide tubes connected to an ergonomically shaped handle. The metacarpal drill guide is used to guide the two metacarpal half pins 25 into their correct orientation and spacing while they are being threaded into the shaft of the second metacarpal 17. The radial drill guide will be one size only with bore diameters slightly larger than 3.0 mm to allow for passage of the radial half pins. The radial drill guide will preferably be a molded plastic part consisting of three equally spaced parallel drill guide tubes connected to an ergonomically shaped handle. The radial drill guide is used to position the three radial half pins 21 into their correct orientation and spacing while they are being threaded into the shaft of the distal radius 13. The ball end type hex wrench will be a standard 5/32 inch hex and will fit all of the socket head fasteners on both the fixator 11 and the alignment table 2.11. The pin end caps will be "one size fits all." The metacarpal and radial drill guides are preferably fabricated from injection molded 33% glass fiber reinforced PPA resin conforming to ASTM D 5336. The ball end type hex wrench is preferably fabricated from 303 stainless steel, conforming to ASTM A 582, type 303, with a molded plastic handle. The half pin end caps are preferably molded plastic.

The preferred embodiment of the method of externally manipulating, reducing, and stabilizing a Colles' type distal radial fracture or the like of the present invention normally starts with the step of securing bone pins (e.g., the half pins 21, 25) to first and second bone elements (e.g., the radius 13 and second metacarpus 17) on opposite sides of a joint (e.g., the wrist joint 15). The half pins 21, 25 are secured to the radius 13 and second metacarpus 17 in any typical, well known manner, such as by being "drilled" into the respective bones using a rotary drill or the like, guided by radial and metacarpal drill guides when desired by the surgeon, etc., as will now be apparent to those skilled in the art.

Normally, the fracture is manipulated and reduced after the half pins 21, 25 are secured to the radius 13 and the second metacarpus 17. If the external fixation alignment table 2.11 is to be used to manipulate and reduce the fracture, such a table 2.11 is provided, the first body member 2.15 of the alignment table 2.11 is attached to the half pins 21 secured to the radius 13, and the second body member 2.17 of the alignment table 2.11 is attached to the half pins 25 secured to the second metacarpus 17. Then, the first slide 2.19, second slide 2.21, third slide 2.23, first pivot 2.25, and second pivot 2.27 of the alignment table 2.11 can be independently adjusted as needed and/or desired by the surgeon to appropriately manipulate and reduce the fracture.

After the fracture has been appropriately manipulated and reduced, either manually or using the alignment table 2.11, etc., some type of fixation is applied thereto to stabilize the fracture until fracture healing has occurred. If the external fixator 11 is to be used to stabilize the fracture, such a fixator 11 is provided, and the first pivot 27, second pivot 31, third pivot 35, first slide 39, and second slide 41 of the fixator 11 are independently adjusted to position the first and second body members 19, 23 of the fixator 11 in position to engage the half pins 21, 25 secured to the radius 13 and second metacarpus 17. Once the fixator 11 has been adjusted, or simultaneously with the adjustment, the first and second body members 19, 23 of the fixator 11 are attached to the half pins 21, 25. After the external fixator 11 is in place on the half pins 21, 25, the fixator 11 is preferably adjusted to position the flexion/extension hinge pin 61 aligned and coaxial with the anatomic flexion/extension axis of the wrist joint 15 (e.g., with the third axis 36). The fixator 11 is securely locked in place by tightening all of the clamp screws 45, 51, 55, 59, and making the desired adjustments to the flexion/extension stops 63 and then tightening the clamp screws 65. The radial proximal clamps 43 and metacarpal clamp 53 can be rotated 90° relative to the long axis of the fixator 11, or removed from the remainder of the fixator 11, thus allowing the fixator 11 to be clamped onto the half pins 21, 25 after the half pins 21, 25 are already in place on the wrist as will now be apparent to those skilled in the art. The radial proximal clamps 43 are provided as two individually tightened pieces to allow for equal distribution of clamping force on all three radial half pins 21.

If the alignment table 2.11 was used to manipulate and reduce the fracture, once the fixator 11 is secured to the half pins 21, 25, the alignment table 2.11 can be removed from the half pins 21, 25, leaving the fracture secured by the fixator 11 until healing has occurred. The threaded half pins 21, 25 can then be cut to length after removal of the alignment table 2.11, to remove any excess length thereof extending past the fixator 11. Pin end caps are then preferably placed onto the cut ends of the half pins 21, 25 to cover any sharp edges produced during the pin cutting operations. The fixator 11 must remain securely locked in place until fracture healing has occurred, at which time the fixator 11 and half pins 21, 25 can be removed from the patient and disposed of by appropriate means. The fixator 11 and half pins 21, 25 are designed to be single-use-only, disposable devices.

The external fixator device is intended to be a temporary use device to be removed from the patient after sufficient healing of the fracture has occurred.

No bone cement will be used in the implantation of this device.

Additional bone graft material, pins, or wires may be used to aid in stabilization of a particular fracture fragment.

Although the present invention has been described and illustrated with respect to preferred embodiments and preferred uses thereof, it is not to be so limited since modifications and changes can be made therein which are within the full intended scope of the invention.

We claim:

1. An external fixator for securing a Colles' type fracture involving a first bone element on a first side of a joint and a second bone element on a second side of the joint, the fixator comprising:

(a) a first body member fixedly attachable to the first bone element;

(b) a second body member joined to the first body member and fixedly attachable to the second bone element;

(c) a first pivot allowing one of the body members to pivot relative to the other body member about a first axis independently of any other movement thereof;

(d) a second pivot allowing one of the body members to pivot relative to the other body member about a second axis independently of any other movement thereof;

(e) a third pivot allowing one of the body members to pivot relative to the other body member about a third axis independently of any other movement thereof, the third axis being nonconcentric with the second axis;

(f) a first slide allowing one of the body members to translate relative to the other body member along the first axis independently of any other movement thereof; and (g) a second slide allowing one of the body members to translate relative to the other body member along the second axis independently of any other movement thereof.

2. An external fixator for securing a Colles' type fracture involving a first bone element on a first side of a joint and a second bone element on a second side of the joint, the fixator comprising:

(a) a first body member fixedly attachable to the first bone element;

(b) a second body member joined to the first body member and fixedly attachable to the second bone element;

(c) a first pivot allowing one of the body members to pivot relative to the other body member about a first axis independently of any other movement thereof;

(d) a second pivot allowing one of the body members to pivot relative to the other body member about a second axis independently of any other movement thereof;

(e) a third pivot allowing one of the body members to pivot relative to the other body member about a third axis independently of any other movement thereof;

(f) a first slide allowing one of the body members to translate relative to the other body member along the first axis independently of any other movement thereof;

(g) a second slide allowing one of the body members to translate relative to the other body member along the second axis independently of any other movement thereof; and (h) a central block having a first end pivotally attached to the first body member and having a second end pivotally attached to the second body member.

3. The external fixator of claim 2 in which is included a pair of flexion/extension stops adjustably attached relative to the central block and moveable between a first position in which all pivotal movement of the body members about the third axis is prevented, and a second position in which a range of pivotal movement of the body members about the third axis is allowed.

4. The external fixator of claim 2 in which the central block has a rectangular window therethrough for allowing radiographic visualization of the distal end of the first bone element therethrough.

5. An external fixation alignment table for manipulating and reducing a fracture involving a first bone element on a first side of a joint and a second bone element on a second side of the joint, the alignment table comprising:

(a) a base;

(b) a first body member mounted to the base and fixedly attachable to the first bone element;

(c) a second body member mounted to the base and fixedly attachable to the second bone element;

(d) a first slide allowing one of the body members to translate relative to the other body member along a first axis independently of any other movement thereof;

(e) a second slide allowing one of the body members to translate relative to the other body member along a second axis independently of any other movement thereof;

(f) a third slide allowing one of the body members to translate relative to the other body member along a third axis independently of any other movement thereof;

(g) a first pivot allowing one of the body members to pivot relative to the other body member about the second axis independently of any other movement thereof; and (h) a second pivot allowing one of the body members to pivot relative to the other body member about the third axis independently of any other movement thereof.

6. The external fixation alignment table of claim 5 in which the base includes a baseplate and an armrest plate attachable to the baseplate in a first position for supporting a patient's right forearm and in a second position for supporting a patient's left forearm.

7. The external fixation alignment table of claim 6 in which the armrest plate is adjustable in both vertical and horizontal directions on the baseplate.

8. The external fixation alignment table of claim 5 in which the first slide includes a manually rotatable crankshaft, the rotation of which causes one of the body members to translate relative to the other body member along the first axis independently of any other movement thereof.

9. The external fixation alignment table of claim 5 in which said second slide includes a manually rotatable crankshaft, the rotation of which causes one of the body members to translate relative to the other body member along the second axis independently of any other movement thereof.

10. The external fixation alignment table of claim 5 in which said third slide includes a manually rotatable crankshaft, the rotation of which causes one of the body members to translate relative to the other body member along the third axis independently of any other movement thereof.

11. The external fixation alignment table of claim 5 in which said first pivot includes a manually rotatable crankshaft, the rotation of which causes one of the body members to pivot relative to the other body member about the second axis independently of any other movement thereof.

12. The external fixation alignment table of claim 5 in which the first pivot includes a slide allowing translation of one of the body members relative to the other body member along a longitudinal axis out of plane with the first axis.

13. The external fixation alignment table of claim 5 in which said second pivot includes a manually rotatable crankshaft, the rotation of which causes one of the body members to pivot relative to the other body member about the third axis independently of any other movement thereof.

14. A method of externally manipulating, reducing, and stabilizing a Colles' type fracture involving a first bone element on a first side of a joint and a second bone element on a second side of the joint, the method comprising the steps of:

a) securing bone pins to the first and second bone elements on opposite sides of the joint;

b) providing an external fixation alignment table comprising:
  i. a base;
  ii. a first body member mounted to the base of the alignment table;

iii. a second body member mounted to the base of the alignment table;
iv. a first slide allowing one of the body members of the alignment table to translate relative to the other body member of the alignment table along a first axis independently of any other movement thereof;
v. a second slide allowing one of the body members of the alignment table to translate relative to the other body member of the alignment table along a second axis independently of any other movement thereof;
vi. a third slide allowing one of the body members of the alignment table to translate relative to the other body member of the alignment table along a third axis independently of any other movement thereof;
vii. a first pivot allowing one of the body members of the alignment table to pivot relative to the other body member of the alignment table about the second axis independently of any other movement thereof; and
viii. a second pivot allowing one of the body members of the alignment table to pivot relative to the other body member of the alignment table about the third axis independently of any other movement thereof;

(c) attaching the first body member of the alignment table to the bone pins secured to the first bone member;

(d) attaching the second body member of the alignment table to the bone pins secured to the second bone member;

(e) then independently adjusting the first, second and third slides, and the first and second pivots of the alignment table to manipulate and reduce the fracture;

(f) providing an external fixator comprising:
 i. a first body member;
 ii. a second body member joined to the first body member of the fixator;
 iii. a first pivot allowing one of the body members of the fixator to pivot relative to the other body member of the fixator about a first axis independently of any other movement thereof;
 iv. a second pivot allowing one of the body members of the fixator to pivot relative to the other body member of the fixator about a second axis independently of any other movement thereof;
 v. a third pivot allowing one of the body members of the fixator to pivot relative to the other body member of the fixator about a third axis independently of any other movement thereof;
 vi. a first slide allowing one of the body members of the fixator to translate relative to the other body member of the fixator along the first axis independently of any other movement thereof; and
 vii. a second slide allowing one of the body members of the fixator to translate relative to the other body member of the fixator along the second axis independently of any other movement thereof;

(g) then independently adjusting the first, second and third pivots, and the first and second slides of the fixator to position the first and second body members of the fixator in position to engage the bone pins secured to the first and second bone elements;

(h) attaching the first and second body members of the fixator to the bone pins secured to the first and second bone elements; and (i) then removing the alignment table from the first and second bone elements, leaving the fracture secured by the fixator.

* * * * *